US006368141B1

(12) United States Patent
VanAntwerp et al.

(10) Patent No.: US 6,368,141 B1
(45) Date of Patent: Apr. 9, 2002

(54) INSERTION SET FOR A TRANSCUTENOUS SENSOR WITH CABLE CONNECTOR LOCK MECHANISM

(76) Inventors: Nannette M. VanAntwerp, 24101 W. Del Monte Dr., #418, Valencia, CA (US) 91355; Edgardo C. Halili, 18435 Keswick St., #20, Reseda, CA (US) 91335

(*) Notice: Subject to any disclaimer, the term of this patent is extended or adjusted under 35 U.S.C. 154(b) by 0 days.

(21) Appl. No.: 09/346,835

(22) Filed: Jul. 2, 1999

Related U.S. Application Data

(62) Division of application No. 08/871,831, filed on Jun. 9, 1997, now Pat. No. 5,954,643.

(51) Int. Cl.⁷ .................... H01R 13/627; H01R 33/20
(52) U.S. Cl. .................... 439/353; 439/676; 439/909
(58) Field of Search .................. 439/353, 677, 439/909, 676, 660; 600/323, 316

(56) References Cited

U.S. PATENT DOCUMENTS

| 3,921,631 A | 11/1975 | Thompson |
| 4,235,234 A | 11/1980 | Whitney et al. |
| 5,249,576 A | * 10/1993 | Goldberger ............... 600/323 |
| 5,299,571 A | 4/1994 | Mastrototaro ............. 128/634 |
| 5,339,810 A | * 8/1994 | Ivers ....................... 600/340 |
| 5,390,671 A | 2/1995 | Lord et al. ............... 128/635 |
| 5,713,869 A | 2/1998 | Morejan ................... 604/174 |
| 5,954,643 A | * 9/1999 | VanAntwerp et al. ...... 600/316 |

FOREIGN PATENT DOCUMENTS

WO 9115993 10/1991

* cited by examiner

Primary Examiner—Neil Abrams

(57) ABSTRACT

An improved insertion set is provided for transcutaneous placement of a sensor such as a glucose sensor at a selected site within the body of a patient. The insertion set comprises a mounting base defining an upwardly open channel for receiving and supporting a flexible thin film sensor, in combination with a cap assembled with said mounting base to capture and retain a proximal end of the sensor within said channel. The sensor further includes a distal segment with sensor electrodes thereon which protrudes from the mounting base for transcutaneous placement, wherein the sensor distal segment is slidably carried by a slotted insertion needle fitted through the assembled base and cap. Placement of the insertion set against the patient's skin causes the insertion needle to pierce the skin to carry the sensor electrodes to the desired subcutaneous site, after which the insertion needle can be slidably withdrawn from the insertion set. The mounting base further includes a fitting and related snap latch members for mated slide-fit releasable coupling of conductive contact pads on a proximal end of the sensor to a cable connector for transmitting sensor signals to a suitable monitoring device.

10 Claims, 7 Drawing Sheets

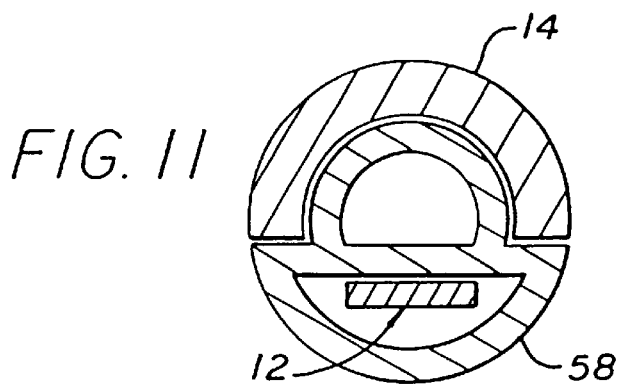
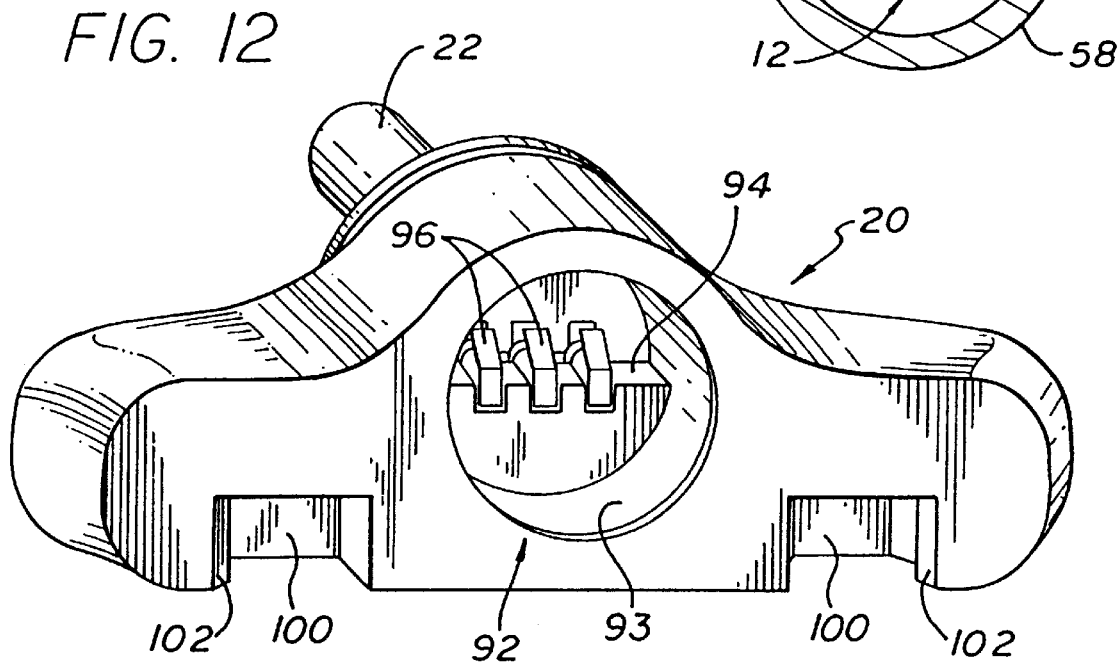
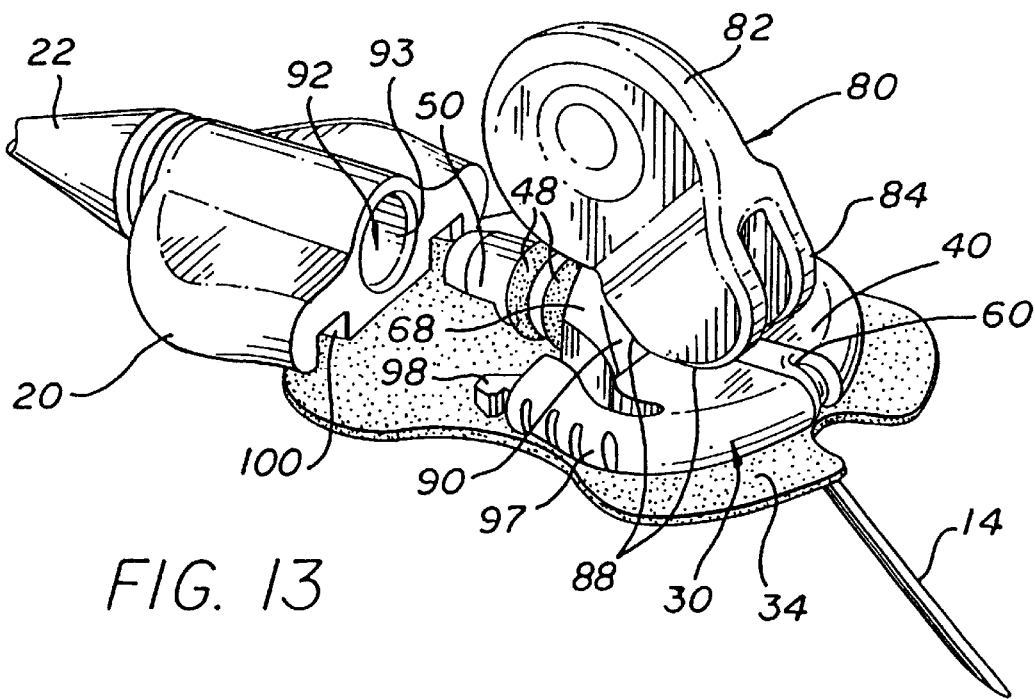

INSERTION SET FOR A TRANSCUTENOUS SENSOR WITH CABLE CONNECTOR LOCK MECHANISM

RELATED APPLICATIONS

This is a division of application Ser. No. 08/871,831 filed on Jun. 9, 1997, now U.S. Pat. No. 5,954,643,

BACKGROUND OF THE INVENTION

This invention relates generally to devices and methods for placing a sensor at a selected site within the body of a patient. More particularly, this invention relates to an improved and relatively simple insertion set for quick and easy transcutaneous placement of a flexible thin film sensor of the type used, for example, to obtain blood glucose readings.

In recent years, a variety of electrochemical sensors have been developed for a range of applications, including medical applications for detecting and/or quantifying specific agents in a patient's blood and other body fluids. As one example, glucose sensors have been developed for use in obtaining an indication of blood glucose levels in a diabetic patient. Such readings can be especially useful in monitoring and/or adjusting a treatment regimen which typically includes regular administration of insulin to the patient. In this regard, blood glucose readings are particularly useful in conjunction with semi-automated medication infusion pumps of the external type, as generally described in U.S. Pat. Nos. 4,562,751; 4,678,408; and 4,685,903; or automated implantable medication infusion pumps, as generally described in U.S. Pat. No. 4,573,994.

Relatively small and flexible electrochemical sensors have been developed for subcutaneous placement of sensor electrodes in direct contact with patient blood or other extracellular fluid, wherein such sensors can be used to obtain periodic readings over an extended period of time. In one form, flexible transcutaneous sensors are constructed in accordance with thin film mask techniques wherein an elongated sensor includes thin film conductive elements encased between flexible insulative layers of polyimide sheet or similar material. Such thin film sensors typically include exposed electrodes at a distal end for subcutaneous placement in direct contact with patient blood or the like, and exposed conductive contact pads at an externally located proximal end for convenient electrical connection with a suitable monitoring device. Such thin film sensors hold significant promise in patient monitoring applications, but unfortunately have been difficult to place transcutaneously with the sensor electrodes in direct contact with patient blood or other body fluid. Improved thin film sensors and related insertion sets are described in commonly assigned U.S. Pat. Nos. 5,390,671; 5,391,250; 5,482,473; 5,299,571; 5,586,553 and 5,568,806, which are incorporated by reference herein.

Notwithstanding the foregoing improvements in and to thin film electrochemical sensors and related transcutaneous insertion sets, there exists an on-going need for further improvements in such insertion sets particularly with respect to facilitated and cost efficient manufacture, improvements in quick and easy transcutaneous placement of the thin film sensor, and simplified attachment of the sensor to a conductive cable or the like for coupling of sensor signals to the associated monitoring device. The present invention fulfills these needs and provides further related advantages.

SUMMARY OF THE INVENTION

In accordance with the invention, an improved insertion set is provided for transcutaneously placing a flexible sensor such as a thin film electrochemical sensor at a selected site within the body of a patient. The insertion set comprises a mounting base adapted for seated mounting onto the patient's skin, in combination with a cap for assembly therewith to cooperatively capture and retain the sensor. A distal segment of the sensor with sensor electrodes thereon is slidably carried by a slotted hollow insertion needle fitted through the assembled mounting base and cap for piercing the patient's skin to subcutaneously place the sensor electrodes as the mounting base is pressed onto the patient's skin. The insertion needle can then be slidably withdrawn to leave the sensor electrodes at the desired subcutaneous site. A proximal end of the sensor including conductive contact pads is carried by a cable fitting on the mounting base for slide-fit coupling with a cable connector, with the mounting base and cable connector including snap fit latch members for releasable interconnection.

In the preferred form, the sensor comprises an elongated thin film element with a head at a proximal end thereof including the contact pads seated in a predetermined position and orientation in the cable fitting formed on the mounting base. A proximal segment of the sensor extends from the cable fitting within a recessed channel defined in an upper surface of the mounting base, with the sensor distal segment protruding angularly forwardly and downwardly from the mounting base. The cap is designed for assembly with the mounting base, as by snap fit interconnection therewith, to capture and retain the proximal sensor segment within the recessed channel. In the preferred form, the sensor distal segment and at least a portion of the proximal segment is protectively carried within a cannula. A proximal portion of the cannula is seated within the channel, and a distal cannular portion extends from the mounting base and is slidably carried by the slotted insertion needle as described in U.S. Pat. No. 5,586,553. The insertion needle is slidably fitted through the assembled mounting base and cap, and is connected at its upper end to an enlarged hub for facilitated manipulation thereof. The hub includes keyed alignment surfaces which cooperate with associated alignment or guide surfaces on the assembled base and cap to prevent or minimize needle rotation relative to the sensor and to guide the needle during slide-fit engagement and disengagement therewith.

The cable fitting formed on the mounting base is sized and shaped for slide-fit coupling with a matingly shaped fitting formed on the cable connector, for electrically coupling the sensor contact pads with individual associated conductors of an electrical cable. In the preferred form, the mounting base includes at least one and preferably a plurality of latch arms for snap fit engagement with latch recesses formed on the cable connector to couple the mounting base and cable connector together with their respective fittings properly engaged.

In use, the snap fit latch members permit quick and easy connection of the insertion set mounting base to the cable connector. The insertion set can then be pressed against the patient's skin so that the insertion needle pierces the skin and carries the cannula with sensor distal segment therein to the desired subcutaneous position. The mounting base is then affixed to the skin, as by suitable adhesive means, and the insertion needle is withdrawn from the patient leaving the cannula and the sensor therein at the selected insertion site. When it is necessary or appropriate to replace with sensor, the used insertion set can be simply removed from the patient to withdraw the sensor from the patient's skin, followed by detachment of the insertion set from the cable connector for disposal thereof. A replacement insertion set is then coupled to the cable connector and transcutaneously placed on the patient as described above.

Other features and advantages of the invention will become more apparent from the following detailed description, taken in conjunction with the accompanying drawings which illustrate, by way of example, the principles of the invention.

BRIEF DESCRIPTION OF THE DRAWINGS

The accompanying drawings illustrate the invention. In such drawings:

FIG. 11 is an enlarged sectional view taken generally on the line 11—11 of FIG. 10;

FIG. 12 is a front end perspective view of the cable connector of FIGS. 1 and 2;

FIG. 13 is an exploded perspective view illustrating assembly of the cable connector with the insertion set;

DETAILED DESCRIPTION OF THE PREFERRED EMBODIMENT

Figure 1:
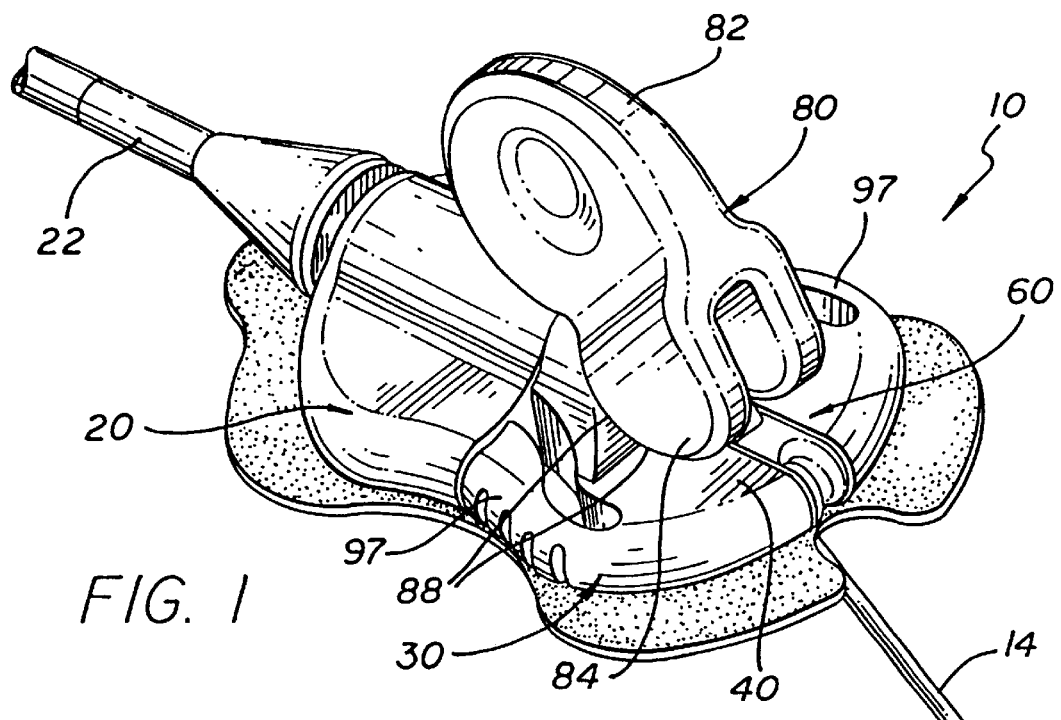
FIG. 1 is a fragmented perspective view illustrating a sensor insertion set embodying the novel features of the invention, wherein the insertion set is depicted in assembled relation with a cable connector.
Figure 2:
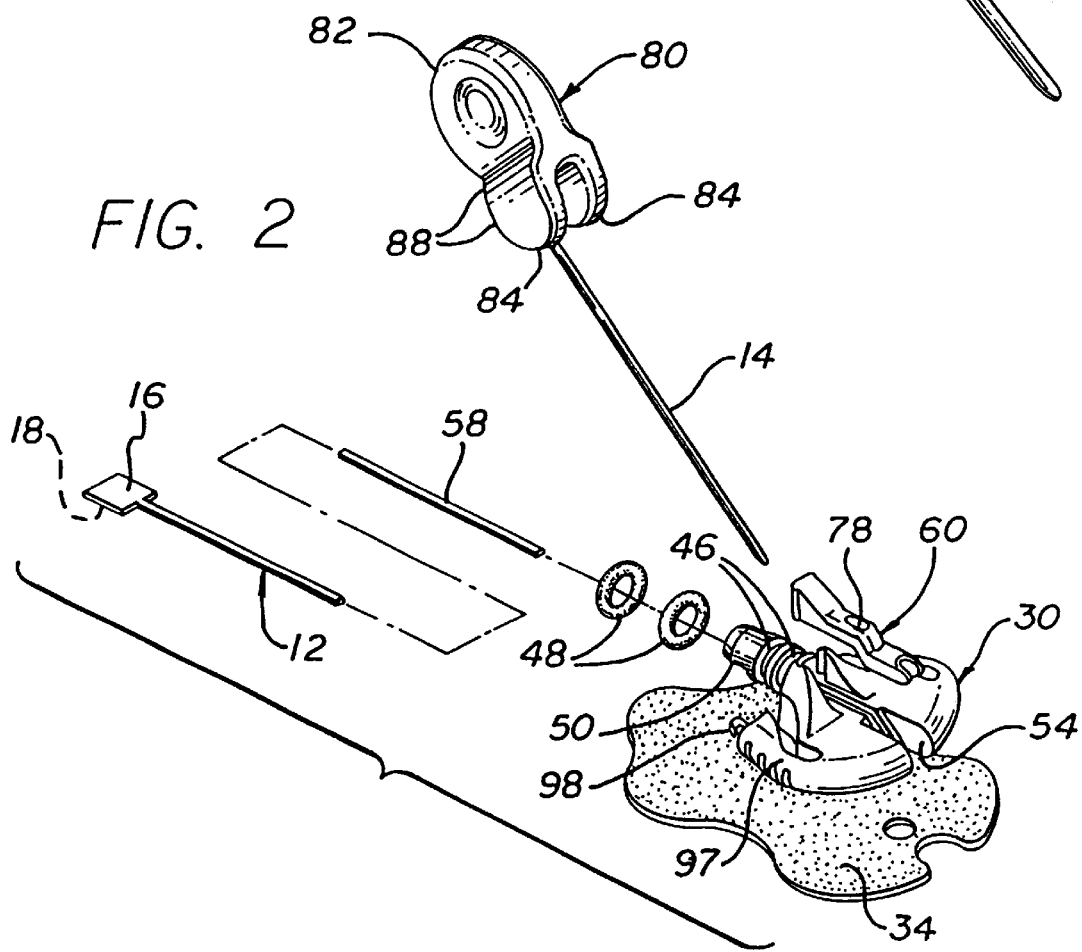
FIG. 2 is an exploded perspective view of the insertion set.

As shown in the exemplary drawings, an improved insertion set referred to generally in FIGS. 1 and 2 by the reference numeral 10 is provided for placing a biological sensor 12 (FIG. 2) in a selected transcutaneous position on a patient. The insertion set 10 includes an insertion needle 14 for placing a distal end segment of the sensor 12 having sensor electrodes 15 thereon (FIG. 3) in a selected subcutaneous position in direct contact with patient blood or other body fluid. The insertion set further supports the sensor 12 for quick and easy coupling of a proximal end or head 16 having conductive contact pads 18 thereon (FIG. 3) with a cable connector 20 (FIG. 1) for coupling sensor signals in turn via an electrical cable 22 to a suitable monitoring device (not shown).

The insertion set 10 of the present invention is particularly designed for facilitating quick and easy transcutaneous placement of a flexible thin film electrochemical sensor of the type used for monitoring specific blood parameters representative of patient condition. The insertion set 10 is designed to place the sensor 12 subcutaneously or at another selected site within the body of a patient, in a manner minimizing patient discomfort and trauma. In one preferred application, the sensor 12 may be designed to monitor blood glucose levels, and may be used in conjunction with automated or semi-automated medication infusion pumps of the external or implantable type as described in U.S. Pat. Nos. 4,562,751; 4,678,408; 4,685,903; and 4,573,994, to deliver insulin to a diabetic patient. However, it will be understood that the sensor may be designed to monitor other patient body fluid parameters for other applications. Further, is will be understood that the term "patient" can be broadly construed to encompass humans and other animals, and that the term "blood" encompasses patient blood and other extracellular patient fluids.

Figure 3:
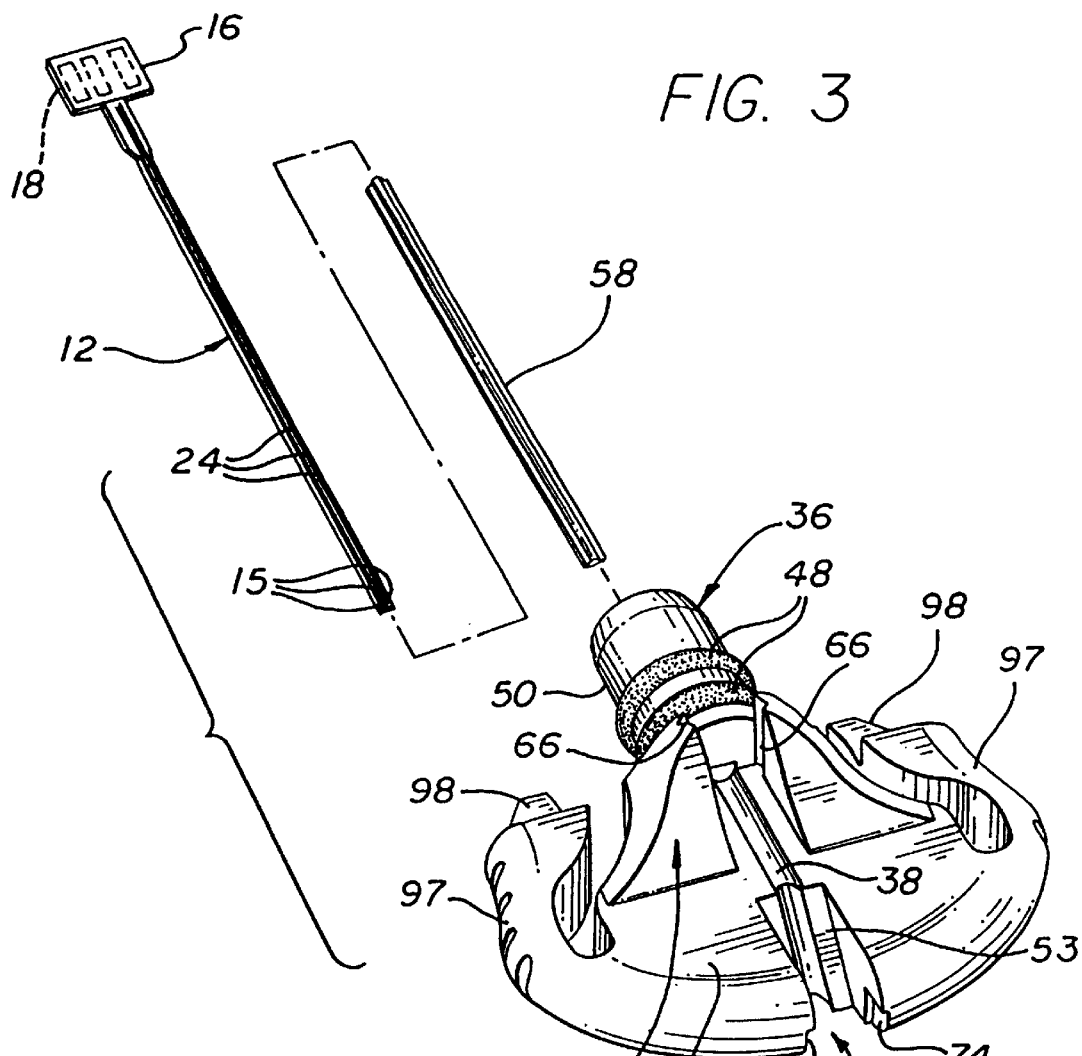
FIG. 3 is an enlarged and exploded perspective view showing assembly of the insertion set components, and depicting an upper side of an insertion set mounting base.
Figure 4:
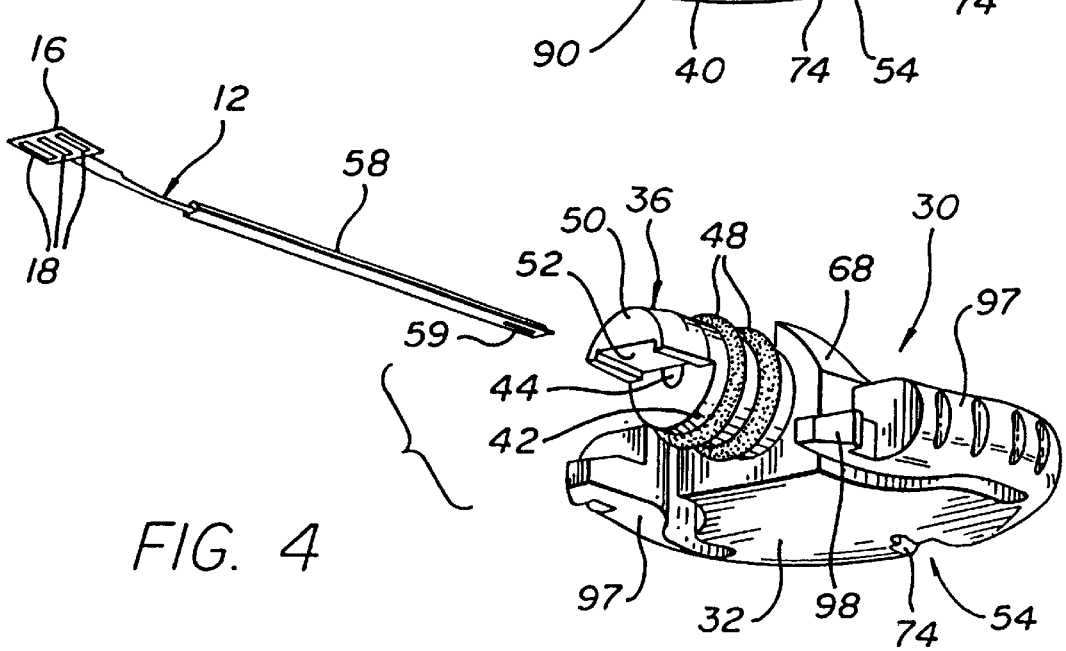
FIG. 4 is an exploded perspective view showing assembly of the insertion set components, depicting an underside of the mounting base.
Figure 5:
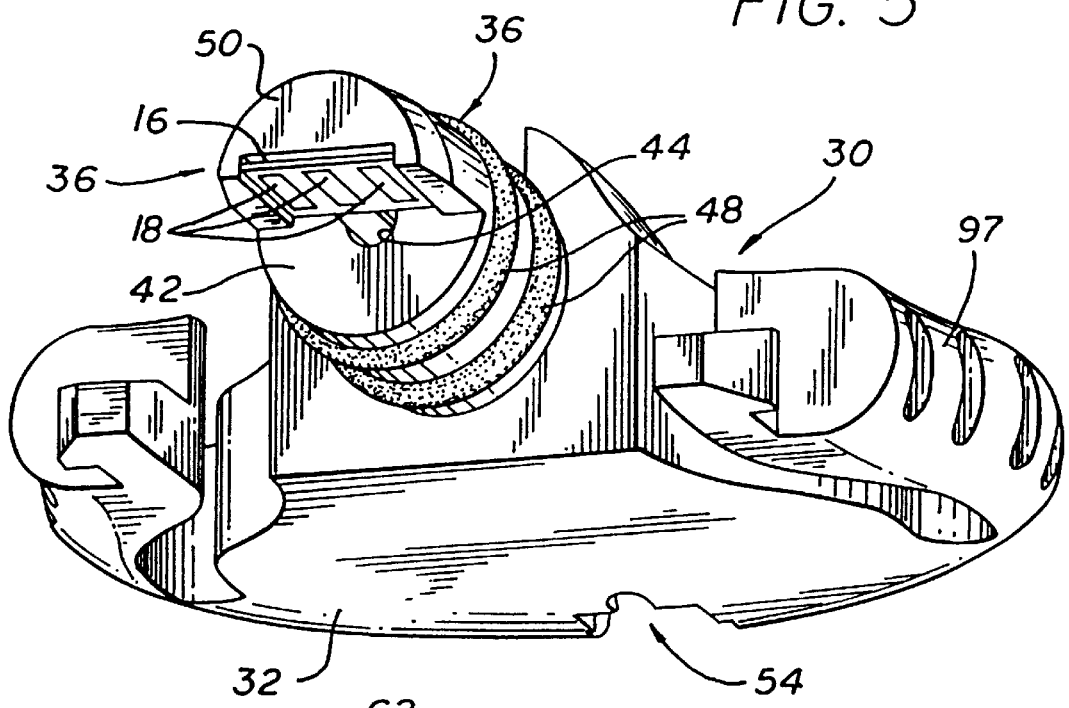
FIG. 5 is an underside perspective view of the mounting base shown in FIG. 4, showing a proximal end or head of a flexible thin film sensor seated on the mounting base.

As shown best in FIGS. 2–4, the flexible thin film sensor 12 comprises a relatively thin and elongated element which can be constructed according to so-called thin film mask techniques to include elongated conductive elements 24 (FIG. 3) embedded or encased between layers of a selected insulative sheet material such as polyimide film or sheet. The proximal end or head 16 of the sensor 12 is relatively enlarged and defines the conductive contact pads 18 which are exposed through the insulative sheet material for electrical connection to the cable 22, as will be described in more detail. An opposite or distal end segment of the sensor 12 includes the corresponding plurality of exposed sensor electrodes 15 for contacting patient body fluid when the sensor distal segment is placed into the body of the patient. The sensor electrodes 15 generate electrical signals representative of patient condition, wherein these signals are transmitted via the contact pads 18 and the cable 22 to an appropriate monitoring device (not shown) for recordation and/or display to monitor patient condition. Further description of flexible thin film sensors of this general type may be found in U.S. Pat. No. 5,391,250, which is incorporated by reference herein.

The sensor 12 is carried by the insertion set 10 which is adapted for placement onto the skin of a patient (FIGS. 14–15) at the selected insertion site. As shown in FIGS. 1–7, the insertion set 10 generally comprises a compact mounting base 30 having a generally planar or flat underside surface 32 (FIGS. 4–5) attached to an adhesive patch 34 for press-on adhesive mounting onto the patient's skin. The mounting base 30 is conveniently and economically constructed as a unitary molding of lightweight plastic to include a rear cable fitting 36 for slide-fit coupling with the cable connector 20. The rear cable fitting 36 cooperates with an upwardly open recessed groove or channel 38 formed in an upper surface 40 of the mounting base 30 (FIGS. 2, 3, 6 and 7) to receive and support the sensor 12.

More particularly, FIGS. 2–5 show the rear cable fitting 36 of the mounting base 30 to comprise a rearwardly projecting tubular element 42 defining a central bore 44 aligned generally coaxially with a rearward end of the recessed channel 38. The tubular element 42 includes external grooves 46 (FIG. 2) for receiving seal rings 48 adapted for sealed slide-fit engagement with the cable connector 20, as will be described. Importantly, the rearward end of the tubular element 42 terminates in a generally D-shaped or half-circle fitting key 50 formed as a rearward extension thereof, and which incorporates a shallow recessed flat or seat 52 formed at the rearward end of the bore 44. This recessed seat 52 is sized and shaped to receive and support the proximal head 16 of the sensor 12, with a proximal end of the elongated sensor 12 extending from said head 16 through the bore 44 and lying within the recessed channel 38. In the preferred form, the head 16 of the sensor 12 is secured and seated (FIG. 5) within the recessed seat 52 by means of a suitable adhesive or the like. In addition, subsequent to placement of the sensor 12 through the bore 44, in the preferred form, the bore 44 is hermetically sealed with a suitable sealant such as curable silicone sealer or the like. For facilitated slide-fit engagement with the cable connector 20, the seat 52 is formed to ramp angularly rearwardly and upwardly from a central axis of the bore 44, thereby supporting the sensor head 16 with the contact pads 18 presented downwardly and angularly rearwardly.

Figure 6:
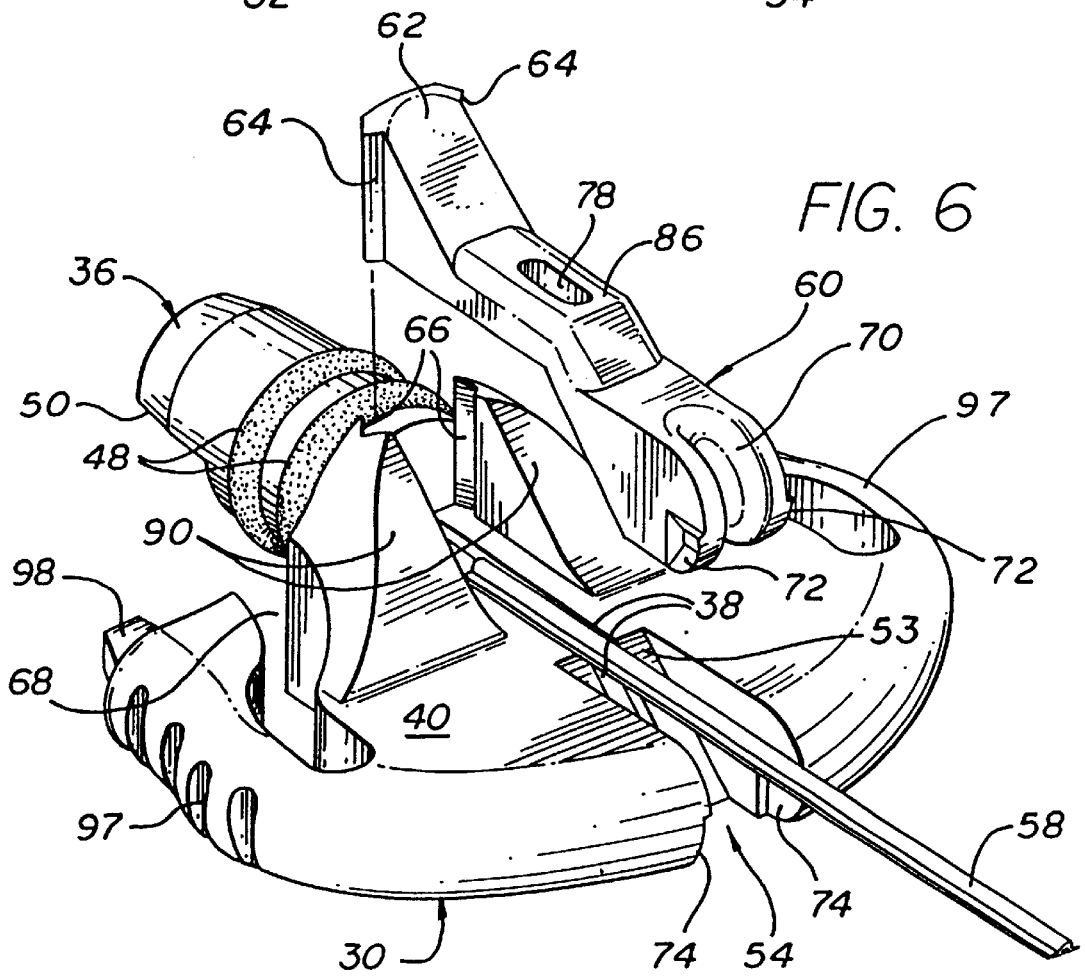
FIG. 6 is another exploded perspective view illustrating assembly of a retainer cap on an upper side of the mounting base.
Figure 7:
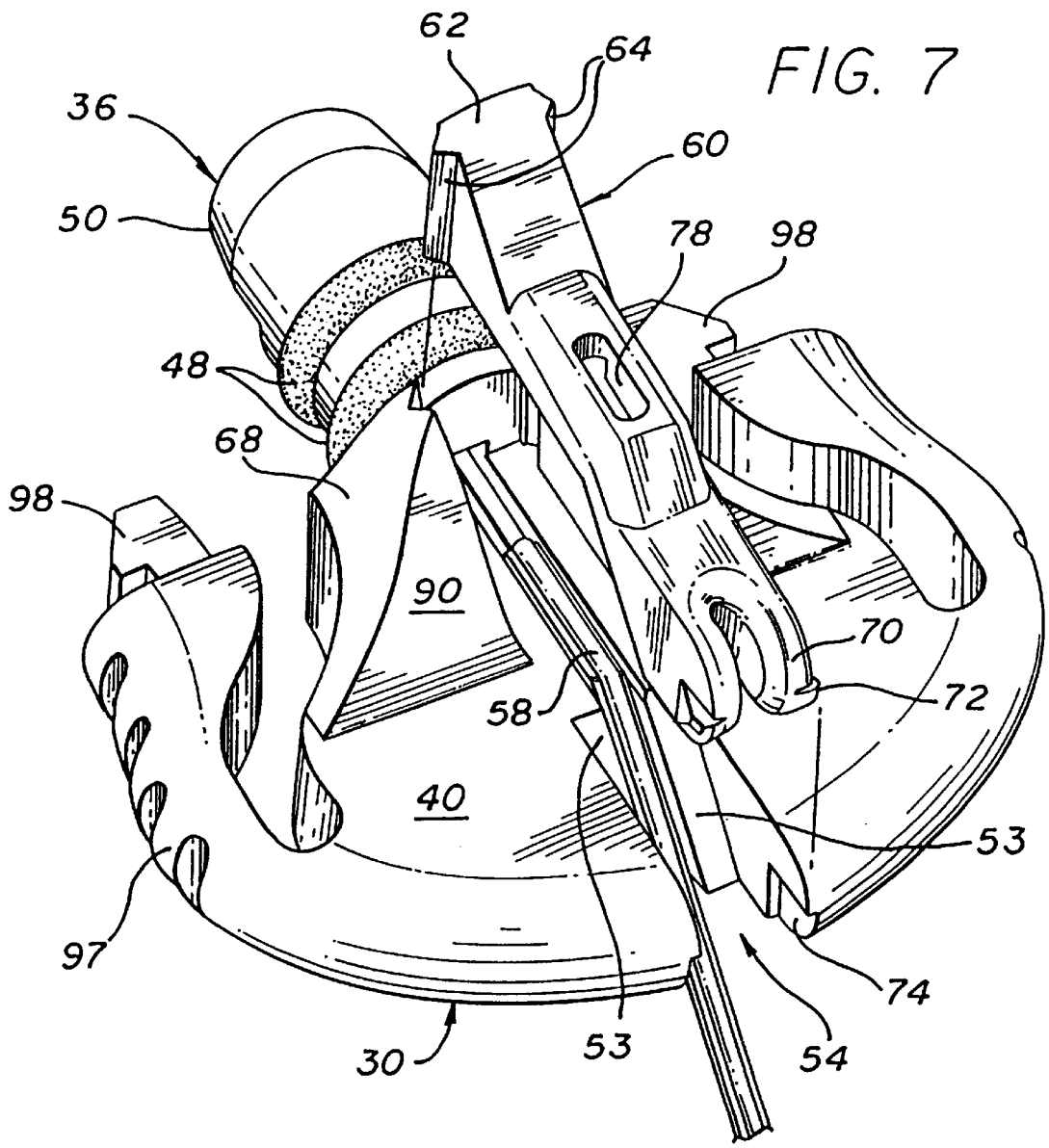
FIG. 7 is an exploded perspective view similar to FIG. 6, and depicting further assembly of the retainer cap with the mounting base.

The recessed channel 38 in the mounting base 30 thus receives and supports the proximal segment of the thin film sensor 12. As shown in FIGS. 3, 6 and 7, the recessed channel 38 extends forwardly from the fitting bore 44 with a generally horizontal orientation, and then turns downwardly and forwardly at an angle of about 45 degrees to extend along an angled face 53 within a forwardly open gap 54 formed in the front end or nose of the mounting base. A cannula 58 is slidably fitted over at least a portion of the proximal segment of the sensor 12, to extend also over the distal segment to encase and protect the sensor. In the preferred form, the cannula is constructed from a lightweight plastic material such as a urethane based plastic, and has a double lumen configuration as shown in FIG. 11 with the sensor slidably received within one lumen thereof. The double lumen cannula 58 is especially suited for slide-fit engagement with and disengagement from the insertion needle 14, as will be described in more detail, and includes a window 59 (FIG. 4) to expose the sensor electrodes 15. The specific cannula construction for receiving and supporting the sensor 12, and for slidably interfitting with the insertion needle 14, is shown and described in more detail in U.S. Pat. No. 5,586,553, which is incorporated by reference herein.

Figure 8:
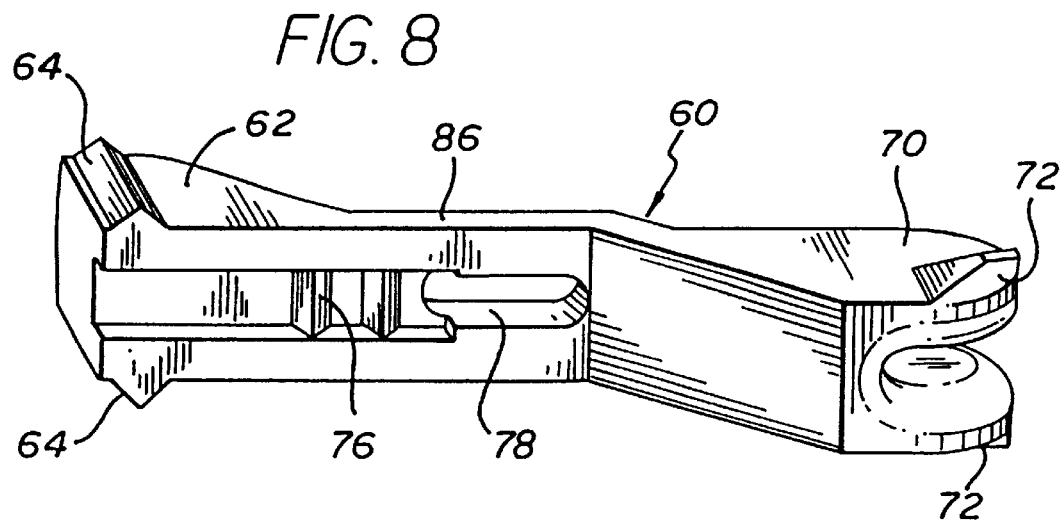
FIG. 8 is an enlarged perspective view showing the underside of the retainer cap of FIGS. 6 and 7.
Figure 9:
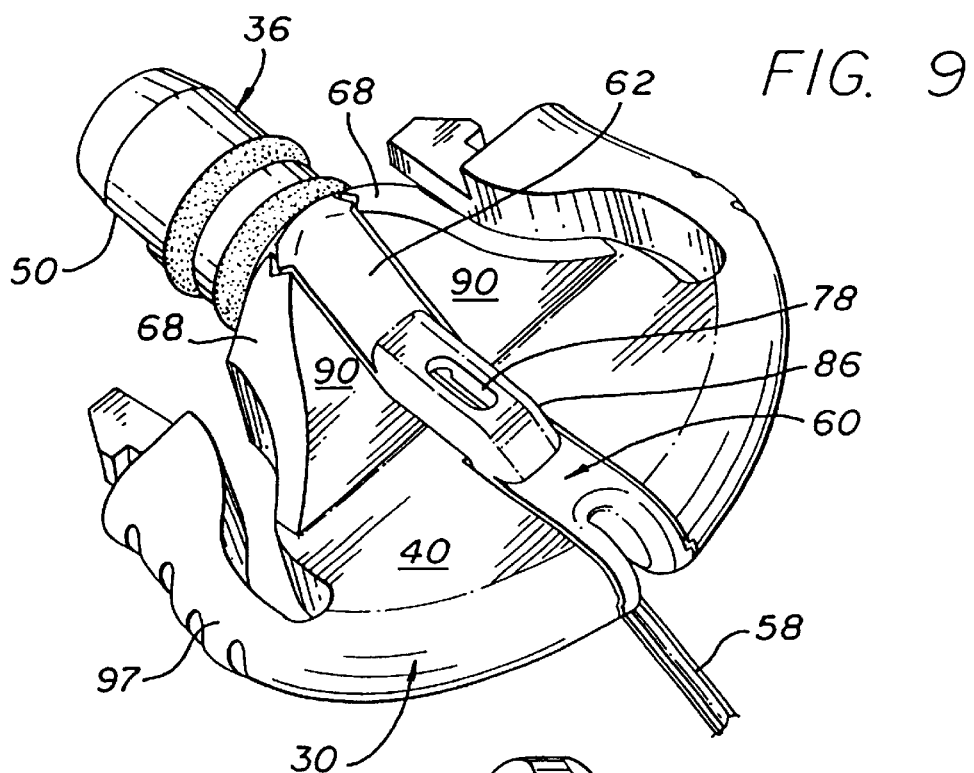
FIG. 9 is a perspective view similar to FIGS. 6 and 7, and showing the retainer cap in assembled relation with the mounting base.

The proximal end of the sensor 12 and the portion of the cannula 58 thereon are folded as shown in FIG. 7 to follow the contour of the mounting base channel 38, so that the distal segment of the sensor and the cannula thereon extend and protrude downwardly and forwardly from the front of the mounting base 30. The sensor and cannula are captured and retained in this orientation by a retainer cap 60 shown in FIGS. 7–9. This retainer cap 60 is also formed conveniently and economically as a lightweight plastic molding and includes means for quick and easy snap fit installation onto the mounting base 30. More specifically, the cap 60 has an elongated and relatively narrow geometry to include a rear head 62 with a pair of upright keys 64 formed on opposite sides thereof for vertical slide-fit reception into a mating pair of keyways 66 formed in upright support brackets 68 on the mounting base 30. A front or nose end 70 of the retainer cap 60 is sized and shaped to fit matingly into the angularly formed gap 54 in the mounting base 30 to retain the cannula 58 and sensor 12 seated in the channel 38 of the ramped face 53. This cap nose 70 includes snap tabs 72 on opposite sides thereof for snap-fit engagement with snap detents 74 lining the gap 54. When the retainer cap 60 is assembled with the mounting base 30, these components cooperatively close the top of the channel 38 to capture and retain the sensor and cannula therein. In this regard, the underside of the cap 60 desirably includes retainer means such as a plurality of retainer teeth 76 (FIG. 8) for frictionally gripping and retaining the cannula with an interference fit within the channel 38. Alternative means can be used to secure the cap 60 to the mounting base 30, such as an adhesive attachment, or ultrasonic bonding means or the like.

Figure 10:
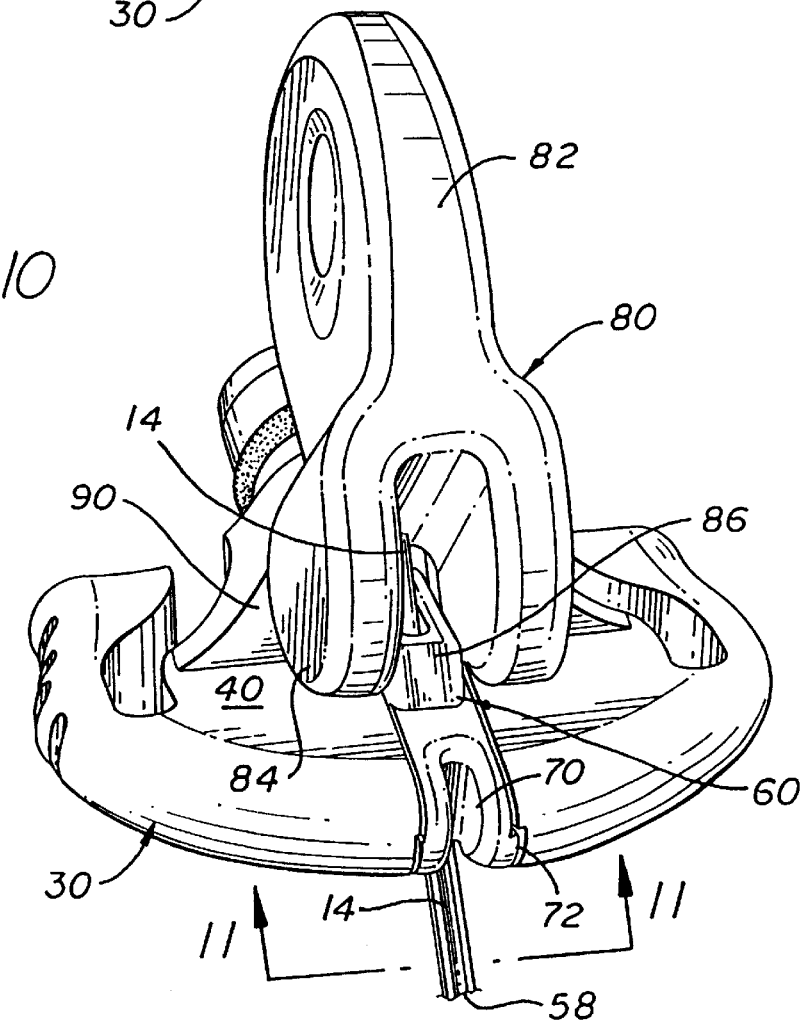
FIG. 10 is a perspective view similar to FIG. 9, and depicting an insertion needle installed on the assembled mounting base and retainer cap.

The retainer cap 60 further defines a needle port 78 (FIGS. 9 and 10) for pass through reception of the insertion needle 14. The insertion needle 14 has a hollow and longitudinally slotted configuration (FIG. 11) with a pointed or sharpened tip and a rear end anchored to an enlarged hub 80. The hub 80 is manually manipulated to fit the needle 14 through the cap port 78, in order to slide the slotted needle into engagement with the cannula 58 within the forwardly and downwardly angled portion of the channel 38. In this regard, the needle port 78 is sized and shaped to orient the insertion needle 14 for proper angular and rotational alignment with the cannula 58 to insure correct slide-fit engagement therebetween.

More particularly, the hub 80 includes an enlarged tab-like wing 82 adapted for easy grasping and handling between the thumb and index finger. This enlarged wing 82 projects upwardly from a bifurcated nose 84 which is sized and shaped to seat onto the mounting base upper surface 40, on opposite sides of a raised central section 86 of the retainer cap 60. The hub nose 84 is contoured to defined keyed alignment or guide surfaces 88 for matingly contacting associated keyed alignment surfaces on the mounting base 30, defined by the upper surface 40 and an angularly presented forward face 90 of the support brackets 68. With this geometry, the hub 80 is slidably displaced against the mounting base 30 with the insertion needle 14 extending into and through the cap port 78 at the correct angular and rotational orientation for slide-fit engagement with and disengagement from the cannula 58. In the preferred form, the insertion needle 14 slidably assembles with the cannula 58 as described in U.S. Pat. No. 5,586,553 to provide a generally circular cross sectional profile (FIG. 11) protruding from the mounting base.

FIGS. 12 and 13 show the cable connector 20 for coupling with the assembled insertion set 10. As shown, the cable connector 20 comprises a compact coupling element which can also be constructed from lightweight molded plastic. The cable connector 20 defines a socket fitting 92 for mating slide-fit engagement with the rear cable fitting 36 of the mounting base 30. This socket fitting 92 has a cylindrical entry portion 93 which merges with a generally D-shaped or half-circle step portion 94 sized to receive the D-shaped key 50 of the fitting 36. As shown, the socket fitting 92 includes a plurality of conductive contacts 96 (FIG. 12) positioned on the step portion 94 for electrically coupled engagement with the contact pads 18 on the sensor 12, when the insertion set 10 and cable connector 20 are coupled together as viewed in FIG. 13. When assembled, the seal rings 48 sealingly engage the entry portion 93 of the socket fitting 92 to provide a sealed connection between the components. Importantly, the D-shaped geometry of the interfitting components 50 and 94 insure one-way interconnection for correct conductive coupling of the cable 22 to the sensor 12.

The insertion set 10 and the cable connector 20 are retained in releasably coupled relation by interengaging snap fit latch members. As shown, the mounting base 30 is formed to include a pair of rearwardly projecting cantilevered latch arms 97 which terminate at the rearward ends thereof in respective undercut latch tips 98. The latch arms 97 are sufficiently and naturally resilient for movement relative to the remainder of the mounting base 30, to permit the latch arms to be squeezed inwardly toward each other. The permissible range of motion accommodates snap fit engagement of the latch tips 98 into a corresponding pair of latch recesses 100 formed in the cable connector 20 on opposite sides of the socket fitting 92, wherein the latch recesses 100 are lined with latch keepers 102 for engaging said latch tips 98. The components can be disengaged for uncoupling when desired by manually squeezing the latch arms 97 inwardly toward each other for release from the latch keepers 102, while axially separating the mounting base 30 from the cable connector 20.

Figure 14:
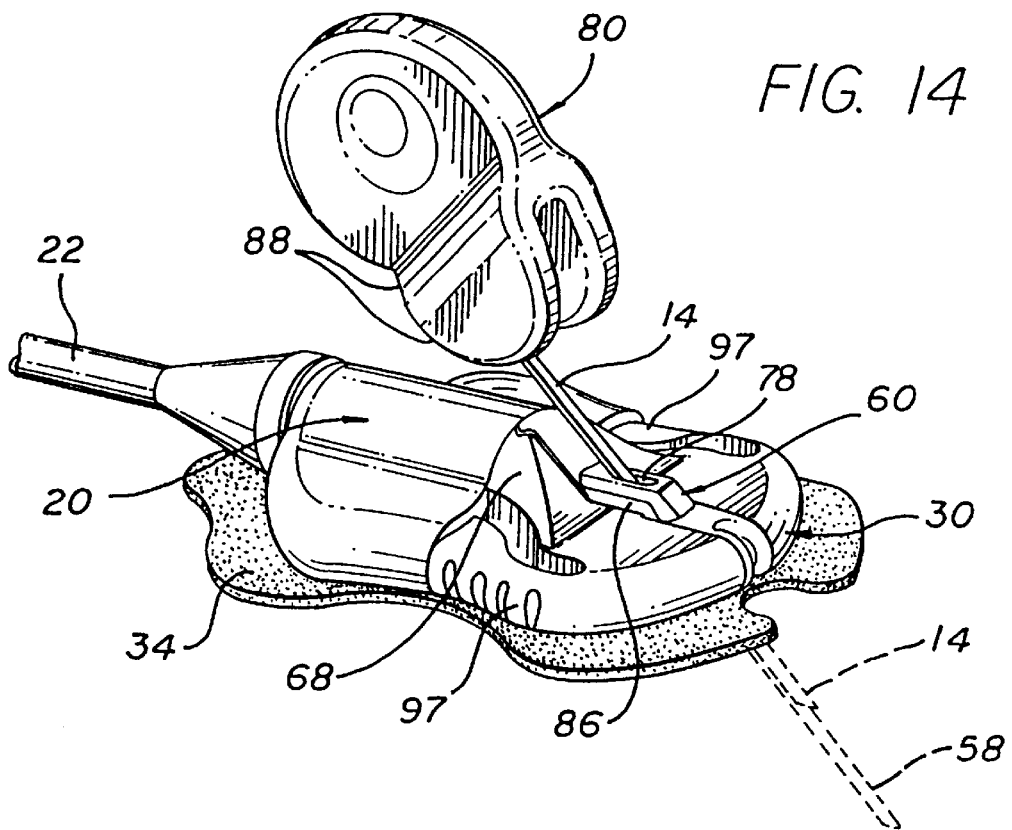
FIG. 14 is a perspective view showing sliding removal of the insertion needle from the insertion set, following placement of the mounting base onto the skin of a patient.
Figure 15:
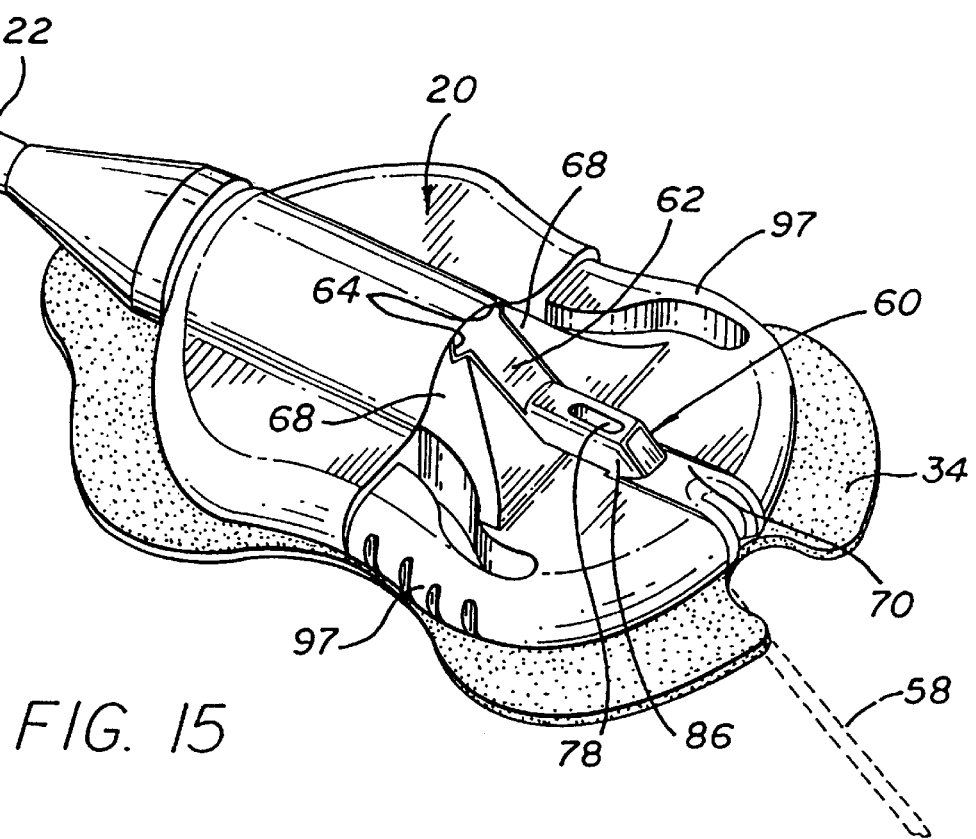
FIG. 15 is a perspective view showing the insertion set and cable connector mounted onto the skin of a patient, following removal of the insertion needle.

The insertion set 10 of the present invention is mounted on the patient's skin quickly and easily to transcutaneously place the sensor 12, as viewed in FIGS. 13–15. The insertion set 10 is initially coupled to the cable connector 20 by engaging the snap fit latch members, with the fitting components 36 and 92 engaged to electrically couple the sensor 12 to the cable 22. The insertion set 10 is then pressed against the patient's skin, typically after removing a protective needle guard (not shown) and a release film (also not shown) from the underside of the adhesive patch 34 to expose a pressure sensitive adhesive thereon. Pressing the set 10 against the skin causes the insertion needle 14 to pierce the skin and thereby carry the cannula 58 with the sensor electrodes 15 thereon to the desired subcutaneous position. The insertion needle 14 is then slidably disengaged from the cannula and sensor by withdrawing the needle from the patient. The insertion set 10 can be affixed more securely to the patient, if desired, by an overdressing (not shown).

When it is necessary or desirable to remove the sensor from the patient, the insertion set is simply removed from the patient's skin to withdraw the sensor from the subcutaneous site. The insertion set 10 is quickly and easily disassembled from the cable connector 20 by appropriate release of the snap fit latch members. A new insertion set 10 can then assembled with the cable connector and quickly placed on the patient to subcutaneously position a new sensor.

A variety of modifications and improvements in and to the transcutaneous insertion set of the present invention will be apparent to those persons skilled in the art. Accordingly, no limitation on the invention is intended by way of the foregoing description and accompanying drawings, except as set forth in the appended claims.

What is claimed is:

1. A cable for connecting a sensor set to a monitor device, wherein the sensor set includes:
    a mounting base adapted for mounting onto a patient's skin, the mounting base including a cable fitting generally at a rear end of the mounting base, wherein the cable fitting of the sensor set includes a tubular element having a central bore formed therein for pass through reception of a portion of the sensor, and wherein the mounting base further includes lock mechanism for releasable coupling to the cable;
    a sensor having at least one sensor electrode thereon, the sensor including at least one contact pad conductively coupled to said electrode, the sensor being coupled to the mounting base;
the cable comprising:
    a cable with two ends; and
    a cable connector connected to one of the two ends of the cable for releasable, interengageable coupling with the lock mechanism on the mounting base of the sensor set, wherein the cable connector includes at least one cable connector contact that is electrically coupled to the at least one contact pad of the sensor when the mounting base of the sensor set is coupled to the cable connector, and wherein the tubular element of the sensor set is for mating with a corresponding tubular recess formed in the cable connector of the cable.

2. The cable of claim 1, wherein the cable fitting of the sensor set includes a recessed seat for supporting and retaining the sensor head, and wherein the recessed seat fits within the a recess in the cable connector.

3. The cable of claim 1, wherein the mounting base of the sensor set and the cable connector of the cable have releasably interengageable snap fit latch members that form the lock mechanism.

4. The cable of claim 1, wherein the cable fitting of the includes a generally D-shaped key formed as a rearward extension of the tubular element, the D-shaped key defining a recessed seat for receiving and supporting the sensor head, and wherein the D-shaped key is for mating with a corresponding D-shaped key recess formed in the cable connector of the cable.

5. The cable of claim 4, wherein the recessed seat of the cable fitting is formed at ramp angle relative to a central axis of the bore, and the cable connector has a corresponding ramp formed in the D-shaped key recess of the cable connector.

6. The cable of claim 1, wherein the mounting base of the sensor set further includes an upwardly open channel formed therein, and the channel extending from the cable fitting to a front end of the mounting base;
    wherein the sensor of the sensor set is a flexible sensor having a head formed generally at a proximal end thereof, a proximal segment extending from said head and a distal segment having the at least one sensor electrode thereon, the head including the at least one contact pad conductively coupled to the electrode; and
    the sensor set further comprising:
        a protective cannula having the sensor distal segment and at a portion of said sensor proximal segment received therein;
        the sensor proximal segment and a portion of the cannula being seated within the channel formed in the mounting base, with the sensor distal segment and the remainder of the cannula protruding from the mounting base;
        a retainer cap mounted on the mounting base to close the channel and to engage the cannula portion therein to capture and retain the cannula portion and the sensor proximal segment within the channel; and
        an insertion needle extending through the assembled retainer cap and mounting base, the cannula including an engagement structure with the needle upon insertion of the needle through the assemble retainer cap and mounting base, the insertion needle being slidably withdrawable from the cannula and from the retainer cap and mounting base.

7. The cable of claim 6, wherein the cable fitting of the sensor set includes a recessed seat for supporting and retaining the sensor head in the sensor set, and wherein the recessed seat fits within the a recess in the cable connector.

8. The cable of claim 6, wherein the mounting base of the sensor set and the cable connector of the cable have releasably interengageable snap fit latch members that form the lock mechanism.

9. The cable of claim 6, wherein the cable fitting of the includes a generally D-shaped key formed as a rearward extension of the tubular element, the D-shaped key defining a recessed seat for receiving and supporting the sensor head, and wherein the D-shaped key is for mating with a corresponding D-shaped key recess formed in the cable connector of the cable.

10. The cable of claim 9, wherein the recessed seat of the cable fitting is formed at ramp angle relative to a central axis of the bore, and the cable connector has a corresponding ramp formed in the D-shaped key recess of the cable connector.

* * * * *